United States Patent [19]

Recchuite

[11] 4,166,795

[45] Sep. 4, 1979

[54] CHEMICAL REACTION PRODUCT OF SULFUR, LARD OIL AND POLYISOBUTYLENE

[75] Inventor: Alexander D. Recchuite, Boothwyn, Pa.

[73] Assignee: Suntech, Inc., Philadelphia, Pa.

[21] Appl. No.: 137,556

[22] Filed: Apr. 26, 1971

[51] Int. Cl.² .................. C10M 1/38; C10M 3/32; C07G 17/00

[52] U.S. Cl. .................. 252/48.6; 260/125; 260/139; 260/399

[58] Field of Search .................. 252/45, 48.6, 79; 260/125, 139, 399

[56] References Cited

U.S. PATENT DOCUMENTS

| | | | |
|---|---|---|---|
| 2,222,643 | 11/1940 | Zimmer | 252/48.6 X |
| 2,312,750 | 3/1943 | Cohen | 252/45 X |
| 2,386,222 | 10/1945 | Lincoln et al. | 252/45 X |
| 2,577,636 | 12/1951 | Sperry | 252/48.6 |
| 3,455,896 | 7/1969 | Herder et al. | 252/48.6 X |

*Primary Examiner*—Irving Vaughn
*Attorney, Agent, or Firm*—J. Edward Hess; Donald R. Johnson; Paul Lipsitz

[57] ABSTRACT

A synthetic sulfurized oil, useful as an additive to lubricants, and especially as a replacement for sulfurized sperm oil, is produced by reaction of sulfur, lard oil and polyisobutylene oligimers containing at least one pair of maximally crowded geminal methyl groups (e.g. "tetraisobutylene"). Preferably, sufficient sulfur to obtain a final sulfurized product containing in the range of about 5–25 weight percent sulfur is reacted with a mixture comprising about 30–90 parts by weight of lard oil and 70–10 parts of the polyisobutylene. Minor amounts (e.g. up to about 15 weight percent) of other unsaturated hydrocarbons (e.g. "$C_{18}$ olefin") can also be present in the mixture.

11 Claims, 1 Drawing Figure

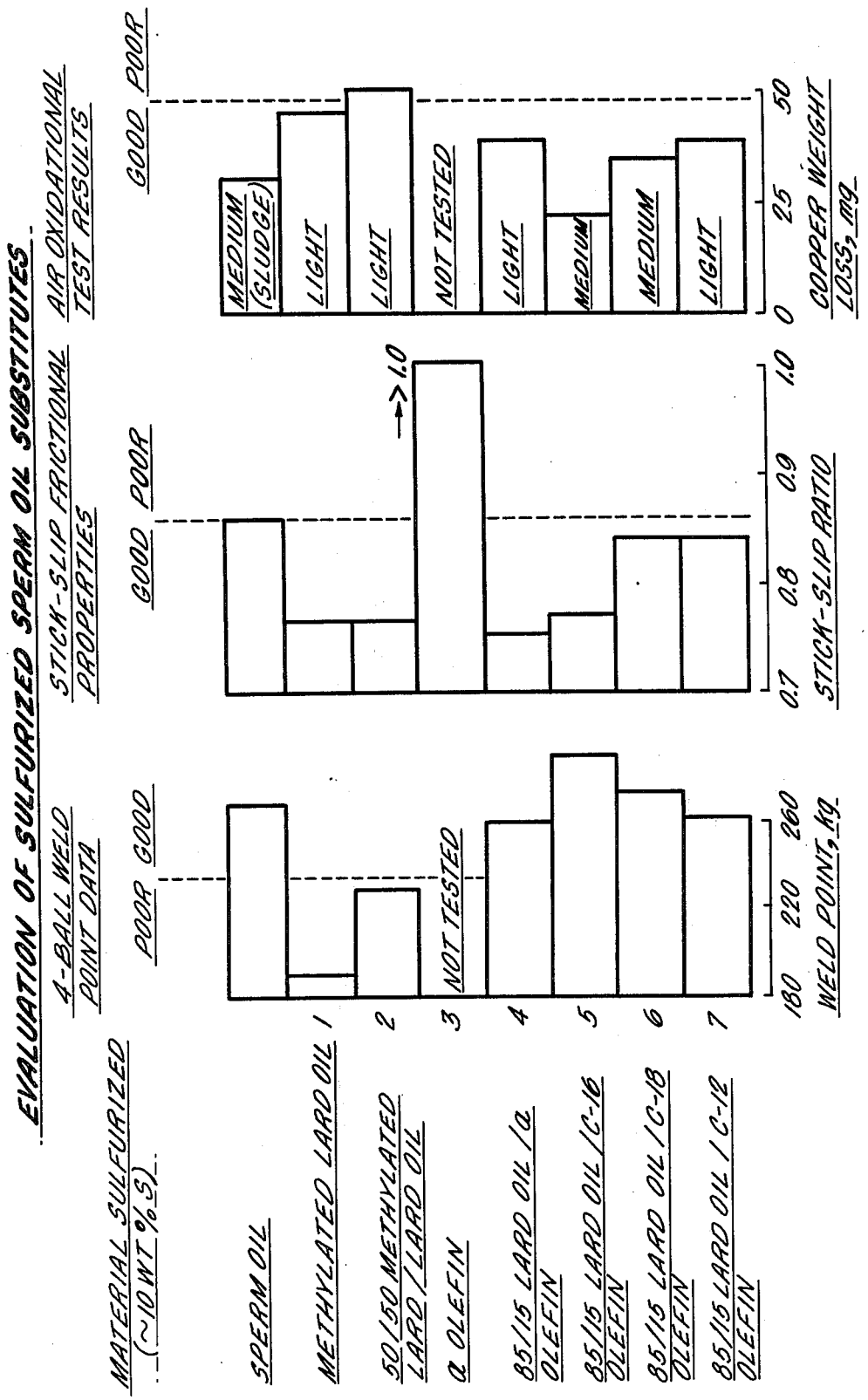

CHEMICAL REACTION PRODUCT OF SULFUR, LARD OIL AND POLYISOBUTYLENE

CROSS REFERENCE TO RELATED APPLICATIONS

In commonly-owned copending application Ser. No. 52,301, filed July 6, 1970, of Gary L. Driscoll, Irl N. Duling and David S. Gates, (now U.S. Pat. No. 3,778,487) novel polyolefin and hydrogenated polyolefin oils are described which are useful as traction fluids, or as components of traction fluids. In particular, said application discloses oils consisting essentially of isobutene oligimers in the $C_{12}$–$C_{48}$ carbon number range. The novel polyolefin oils or the individual olefins therein are also disclosed as being useful as chemical intermediates to prepare novel chemical derivatives.

In commonly-owned application Ser. No. 135,295 of Gary L. Driscoll and Marcus W. Haseltine, Jr., filed on Apr. 19, 1971, and titled "Chemical Reactions of Polyisobutylene" (now U.S. Pat. No. 3,972,941), such chemical derivatives, and their use as traction fluids or as antiwear additives in lubricants are further described. Such oils and olefins are also described in commonly-owned, copending application Ser. No. 052,300, filed July 6, 1970 and titled "Branched Hydrocarbons in the $C_{16}$–$C_{40}$ Range Having Maximally Crowded Geminal Methyl Groups" of Gary L. Driscoll, Irl N. Duling, David S. Gates and Robert W. Warren (now U.S. Pat. No. 3,775,503).

The preparation of a synthetic sulfurized oil, useful as a replacement for sulfurized sperm oil, is disclosed in commonly-owned copending applications of David S. Gates, Paul E. Hagstrom and Marcus W. Haseltine, Jr., titled "Lubrication of Controlled Slip Differential" (Ser. No. 116,841, now U.S. Pat. No. 3,843,534) and Thomas D. Newingham, Alexander D. Recchiute, John Q. Griffith, III and Marcus W. Haseltine, Jr. titled "Lubricant for Controlled Slip Differential" (Ser. No. 116,985, now U.S. Pat. No. 3,825,495), both filed on Feb. 19, 1971. The preparation of such a synthetic sulfurized oil, by coreaction of sulfur, lard oil and polyisobutylene, is also described in the previously cited application of Driscoll and Haseltine, and is also contained in the application of Alexander D. Recchiute, Ser. No. 135,466, now abandoned, filed on or about Apr. 19, 1971 and titled "Process of Sulfurizing Lard Oil and an Olefin and Resultant Product."

The disclosure of all of the above-cited applications (all of which are owned by the Sun Oil Company, as is the present application) is hereby incorporated herein by this reference.

BACKGROUND OF THE INVENTION

In the past sulfurized sperm oil has been used as an additive (usually as a friction modifier) in many lubricant formulations, such as in gear oils, worm and spur gears, automatic transmission fluids, wax lubricants, Permawick lubes for sintered bronze or sintered babbit bearings, and as a cutting oil additive. Sulfurized sperm oil has now become quite expensive (about $.40 per pound) and the present invention is directed to a relatively inexpensive (about $.20 per pound) replacement for sulfurized sperm oil. Sulfurized olefins alone do not have the lubricity necessary for many applications, as is indicated by their high slip/stick ratios. Sulfurized lard oil is not adequately soluble in paraffinic base oils. It has now been found that by sulfurizing a blend of lard oil and polyisobutylene together, a material (or "co-reaction product") is obtained which has good lubricity and is soluble in paraffinic base lube stocks.

SUMMARY OF THE INVENTION

Broadly, the present invention involves novel compositions comprising novel chemical reaction products which can be produced by the action of sulfur or sulfur monochloride on lard oil and the polyolefins or polyolefin oils of the aforementioned applications Ser. No. 52,300 and Ser. No. 52,301. Such co-sulfurized compositions are useful as lubricant additives, particularly in lubricants for tractive drives and limited slip differentials, and are generally useful as a replacement for sulfurized sperm oil.

A novel substitute for sulfurized sperm oil can be obtained by sulfurizing a blend of 90 to 30 parts by weight of lard oil and 10 to 70 parts of an olefin containing 12 to 128 carbon atoms. The sulfurization is carried out using elemental sulfur. Sulfur monochloride can be used for both sulfurizing and chlorinating simultaneously. The sulfurization involves cooking at from 330° to 445° F. for 20 minutes to 10 hours followed by blowing with a gas (preferably, at from 125° to 340° F. for 30 minutes to 20 hours) to remove hydrogen sulfide. With sulfur monochloride, the preferred cooking temperature is in the range of 150°–250° (under pressure if desired). The sulfurized oils can contain from 5 to 25 weight percent sulfur as based on the blend of olefin and lard oil (i.e., 5 to 25 parts by weight of sulfur per 100 parts by weight of the olefin-lard oil blend).

For example, one embodiment of the invention is a composition consisting essentially of a sulfur-containing chemical reaction product of a mixture of lard oil and a branched olefin hydrocarbon having 4 N carbon atoms where N is an integer from 3–32, said olefin hydrocarbon having the formula:

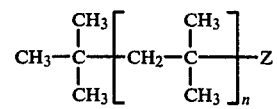

wherein n is an integer from 0 to 29 inclusive, and wherein Z is:

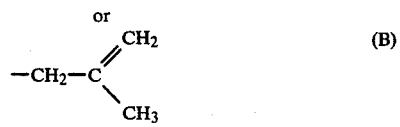

For example, in tetraisobutylene, for one isomer, n is 1 and Z is (D); for another, n is 2 and Z is (B); for another, n is 2 and Z is (A); for another, n is 1 and Z is (C); for another, n is 1 and Z is (E). For triisobutylene, for one isomer, n is 0 and Z is (D); for another, n is 0 and Z is (C) or (E); for another, n is 1 and Z is (A); and for another n is 1 and Z is (B).

The product of the present invention can be produced by blending from 90 to 30 parts of lard oil and from 10 to 70 parts of polyisobutylene, sulfurizing the blend and then blowing the co-sulfurized blend (or co-reaction product) with a gas to remove hydrogen sulfide. The lard oil and olefin generally are blended together at from 65° F. to 340° F. and the sulfur added while the blend is within this temperature range. In general, the preferred process conditions are those taught in the aforementioned application of Recchuite, Ser. No. 135,466, (filed on or about Apr. 19, 1971).

Note that all of the reactions taught in the aforementioned application of Driscoll and Haseltine, Ser. No. 135,295, can be made with any of the above-described olefins (e.g., where n is from 0 to 29 inclusive).

BRIEF DESCRIPTION OF THE DRAWING

The accompanying drawing illustrates certain beneficial properties (related to lubrication and stability) of the synthetic sulfurized oils of the present invention (represented by "85/15 lard oil/$C_{16}$ olefin," Oil Number 5, and "85/15 lard oil/$C_{12}$ olefin," Oil Number 7). The preparation of these two oils is described in the accompanying examples. The FIGURE particularly illustrates the unexpected superiority in the 4-ball weld point test and the air oxidation test (expressed in Copper weight loss) of the sulfurized blend of lard oil and "tetraisobutylene" (i.e., "$C_{16}$ olefin"). Note also that this sulfurized product had better stick-slip frictional properties than any of the sulfurized oils tested excepting for that from the "α-olefin," and the difference in the stick-slip test results for these two oils is so slight as to probably be of no technical significance.

FURTHER DESCRIPTION

The preferred commercial lard oil generally is described as winter grade lard oil. Lard oils suitable for use in this invention are defined in Table I.

TABLE I

| Properties | Preferred Lard Oils | Suitable Lard Oils |
|---|---|---|
| Free Fatty Acids as Oleic | 2–5% | 0.2–20% |
| Saponificaton Number | 192–198 | 192–198 |
| Pour Point (ASTM) | 35–45 | 35–50 |
| Viscosity SUS @ 100° F. | 200–210 | 200–210 |
| Melting Point | 65–75 | 65–75 |
| Sp. Gr. 25° C. | 0.910–0.915 | 0.910–0.915 |
| Iodine Number | 60–75 | 60–75 |

The principal difference between the less preferred grades such as No. 1 lard oil and the preferred grade is in the greater amount of saturated free fatty acids present in the less preferred grades, which can reduce the solubility of the product.

The preferred specifications as reported in Table I include grades which are superior to extra winter strained lard oil in this respect, as well as winter strained lard oil. The polyisobutylene, suitable for use in the present invention, can contain from 12 to 40 carbon atoms, preferably from 12 to 24 carbon atoms, more preferred 16 or 20. The amount of sulfur generally varies from about 5 to 25 percent by weight as based on the blend of lard oil and polyisobutylene.

When an "inactive" sulfurized product is desired, the preferred oils can contain from 6 to 11 percent as based on said blend. Under the reaction conditions specified herein, this amount of sulfur will become chemically bonded in an inactive form. The resultant product containing 6 to 11 percent sulfur, as based on the blend of lard oil and polyisobutylene, is useful as a friction modifier for many applications as well as a cutting oil.

Generally when sulfurized oils are used as cutting oils it is desirable that they contain a relatively large amount of sulfur because it is the sulfur itself which is the most important ingredient due to its function as an antiweld agent. Generally in such cutting oils from 16 to 25 percent sulfur should be present. The sulfur present above about the 11 percent level will usually be in the active form.

The amount of sulfur in a given sample of oil is readily determined by X-ray fluorescence. After the amount of total sulfur is determined 100 g. of the oil sample and 20 g. of copper powder are placed in a tall 250 ml. beaker set up on a hot plate and equipped with a thermometer and an Unger stirrer operated at 1750 rpm. The sample is heated to 350° F. within a 5 minute period and maintained at 350°±5° F. for one hour after which it is cooled and filtered through filter paper to remove the copper powder. The sulfur content of the sample is again determined by X-ray fluorescence which is the inactive sulfur. The loss of sulfur (total minus inactive sulfur) is the amount of active sulfur in the original. The amount of active sulfur in a sulfurized oil being used as a friction modifier should be less than about 2.5%. Generally the friction modifiers of the present invention which contains 6–11% total sulfur will also contain from 1 to 2% active sulfur. The sulfurized cutting oil additives of the present invention which contain from 16 to 25 total sulfur will generally contain from 5 to 18% active sulfur. Generally the sulfur is added to the lard oil-olefin blend over a period of 1 to 60 minutes while the blend is maintained at from 65°–340° F. with constant stirring. The temperature is not particularly critical, the 65° F. represents the softening point of the lard oil and the 340° F. represents the flash point of the olefin.

After addition of sulfur the mixture is cooked. When the product is to be used as a cutting oil the amount of active sulfur present is not critical and a temperature as low as 330° F. may be used. The maximum temperature that should be used in the cooking step is governed by the flash points of the feed components and of the product (typically about 445° F. is a maximum flash point of such mixtures). While pressure apparatus could be used if desired which would raise the maximum possible temperature the reaction is most readily carried out a atmospheric pressure due to economic considerations. With the formulations where a minimum of active sulfur is desired the cooking should be carried out at greater than 365° F. In the case of the formulations where the presence of high amounts of active sulfur can be present there is no advantage in cooking at over 390° F. Generally the cooking is carried out for from 20 minutes to 10 hours.

After cooking the sulfurized oil is blown with a gas to remove $H_2S$. Any gas may be used which dissolves (or otherwise removes) $H_2S$ and does not significantly react with the sulfurized oil. Suitable gases include air, nitrogen, carbon dioxide and gaseous perhalogenated hydrocarbons. Air is preferred for obvious economic considerations. The blowing is most simply carried out by bubbling the gas through the sulfurized oil. Alternatively the oil may be sprayed into the gas or a falling curtain of the oil in the gas may be used. Generally the blowing is carried out at from 125° to 340° F. In the case of the sulfurized oils containing minimal active sulfur the blowing should not be carried out above about 250° F. when air is the gas. When a high sulfur content (16-30%) oil is being made it is preferred to use gas blowing temperatures above 190° F. as this minimizes the active sulfur lost in processing.

The sulfur may be added either as elemental sulfur or sulfur monochloride ($S_2Cl_2$). The elemental sulfur is usually preferred for the low sulfur (6-11%) oils but $S_2Cl_2$ is often preferred for the cutting oil applications because the chlorine also reacts with the oil and serves to improve the antiweld characteristics of the product.

The products of the present invention possess properties not possessed by either sulfurized lard oil or sulfurized olefins or blends of separately sulfurized lard oil and separately sulfurized olefins. The sulfurized lard oil suffers from lack of compatibility with paraffinic lubes. Sulfurized methylated lard oil has somewhat better oil solubility. The sulfurized olefins do not have adequate lubricity as evidenced by their poor stick/slip ratios (static friction/dynamic friction) when used as a lube additive.

The combination of stick/slip and compatibility properties are particularly important in automatic transmission fluids and limited slip differential fluids. Automatic transmission fluids normally contain 75 to 98% of a paraffinic base oil and from 2 to 25% additives. The additives are necessary because no oil alone has all of the viscosity, flash point, foaming and lubricity, etc. properties usually desired in an automatic transmission fluid.

Usually a plurality of additives are used, each specific additive being designed to improve one specific property of the hydrocarbon oil. A composition adapted for use as an automatic transmission fluid will normally have a viscosity of at least 49.0 SUS at 210° F. Moreover the viscosity of the fluid must remain substantially constant during the use of the fluid. It will usually have a viscosity of at least 46.5 SUS after being used in a car which is repeatedly accelerated sufficiently to bring the temperature of the fluid to 300° F. The fluid should have a flash point of at least 320° F. as determined by ASTM D-92. Further descriptions of typical automatic transmission fluid properties are fully set forth in United States Patent No. 3,388,068, issued June 11, 1968, Thomas D. Newingham and U.S. Pat. No. 3,017,361, issued January 16, 1962, John R. Morris et. al.

The sulfurized oils of the present invention are useful as friction modifiers in such fluids to reduce the static friction more than the dynamic friction. Generally the sulfurized oils of the present invention are used at from 1-5% of the overall fluid. A typical automatic transmission fluid might have the following composition: 82.7% solvent refined paraffinic lube having a viscosity of 40 SUS at 210° F., 110 SUS at 100° F., and a viscosity index of about 100, 3% sulfurized oil of Example 3, 0.5% zinc dialkyl dithiophosphonate, 0.5% 4,4-methylenebis (2,6-di-tert-butyl phenol), 0.3% barium alkyl phosphonate (Amoco 121), 1% over-base barium petroleum sulfonate (Bryton Hy Base, base No. about 80) and 15% of a hydrorefined naphthenic lube (as a seal swell agent) containing about 35% gel aromatics and having an SUS viscosity at 100° F. of about 100 SUS.

ILLUSTRATIVE EXAMPLES

EXAMPLE 1

A three-necked, one-liter, round-bottomed flask was equipped with a mechanical stirrer, a gas inlet tube (which also serves for intermittent product removal), and a reflux condenser containing a thermometer which dipped into the liquid layer and was capped with a gas exit tube leading through a mercury bubbler to the atmosphere. Nitromethane (200 ml.) and stannic chloride (5 ml. = 11.15 g.) were added to the flask and the isobutylene flow started. The reaction was maintained at 30°±1° C. with an ice bath. The rate of isobutylene addition was 7.2 g/min. which resulted in 8.5 ml/min. of product (density ~0.85) formation. At 20 min. intervals, the isobutylene feed and the stirrer were stopped and the layers permitted to separate. The top oil layer (170 ml.) was removed and the nitromethane (bottom) layer was returned to the reactor with 5 ml. (3% of product volume) fresh nitromethane added to compensate for solubility losses. After four twenty-minute runs, the reaction was stopped. The catalyst in the nitromethane layer was readily killed with water with some production of HCl fumes. No difficulty with an exotherm was encountered when killing the catalyst. The combined oil layers (665 ml. including 20 ml. nitromethane) were washed with water, with 5% sodium hydroxide solution, and twice more with water. A solvent such as pentane or hexane can be added to facilitate handling.

Although the oil of this example contains all of the novel polyisobutylene oligimers in the series $C_{16}-C_{20}$... $C_{48}+$, fractional vacuum distillation can be used to obtain fractions relatively pure in a given oligimer (e.g. $C_{16}$ or "tetraisobutylene").

In the reaction of this example (and the processes of Ser. Nos. 52,771 (now abandoned); 52,772 (now U.S. Pat. No. 3,655,808); 52,773 (now U.S. Pat. No. 3,657,369) and 53,268 (now abandoned)), small amounts of water in the catalyst and/or feed material can act as a reaction promoter. If extremely pure materials are used in the process, a small amount of water can be added to initiate or hasten the reaction. A lower alcohol (e.g., methanol) or acid (e.g., acetic acid) can also be used as such a promoter. Generally, the reaction rate can be increased (over anhydrous) by addition of 0.1-1.5 moles $H_2O$ per mole of $SnCl_4$.

Polyolefin products, such as that of this example, can contain residual tin and chlorine (e.g., 250-5000 ppm Cl). These elements, particularly the tin, can be present as a metalorganic compound which imparts EP (extreme pressure lubricant) properties to the product. However, if one desires, the chlorine (e.g., 2000 ppm) can be removed from the product by heating the product with calcium oxide (lime) followed by filtration. Mild catalytic hydrogen treatment (e.g. 200 psi. of $H_2$, 200° C., Harshaw NI-0104P catalyst) can also be used to reduce the tin and chlorine content to very low levels (e.g., Cl from 2000 ppm. to 6 ppm) and the resulting polyisobutylene (which can be present with hydrogenated polyisobutylene) can be used to produce the sulfurized product of the present invention.

The process of the present example can also be used to convert butadiene to trans-1,4- and 1,2-polybutadienes. This is surprising since prior art cationic catalyst systems convert butadiene to cyclized polymers. A co-sulfurized product of lard oil and these polybutadienes can be obtained by sulfurization as in the process of Example 3 herein.

EXAMPLE 2

Polyisobutylene oil, produced as in Example 1, was fractionally distilled, at atmospheric pressure, to obtain a product which contained at least 80 weight percent of the C₁₆ isobutylene oligimer (i.e., "tetraisobutylene"). The predominantly C₁₆ fraction boiled in the range of 190°-245° C. and over 90 volume percent boiled at 240° C. Analysis by vapor phase chromatography showed that this predominantly C₁₆ fraction contained less than 10 weight percent C₁₂ oligimer and less than 10 weight percent of the C₂₀ and higher oligimers.

EXAMPLE 3

Twenty-two hundred and sixty ml. of winter strained lard oil were blended with 400 ml. of tetraisobutylene (prepared as in Example 3) in a 5 L kettle equipped with a vibromixer. The mixture was heated to 250° F. and the vibromixer operated at maximum speed. Sulfur (239 g.) was added and the temperature of the mixture raised to 375° F. for two hours. The mixture was then cooled to 200° F. and air was bubbled through the mixture by means of a glass tube at a moderate rate (below that at which splashing and agitation take place) for one hour. The resulting sulfurized oil was analyzed and found to contain 8.23% sulfur. A ten gram portion of the sulfurized oil was dissolved in 100 g. of a commercially available solvent refined paraffinic lube having a viscosity at 210° F. of 40.45 SUS, an ASTM viscosity index of 104 and containing 12% aromatics (by ASTM D2007). The oil solution remained clear with no separation after being tested at 36° F. overnight and for one week at room temperature.

EXAMPLE 4

Winter strained lard oil (2525 ml.) was blended with 450 ml. of 80+% pure triisobutylene (prepared by a distillation similar to that used in Example 6 but at a lower temperature), in a 5 L kettle equipped with a vibromixer. The mixture was heated to 250° F. and the vibromixer operated at maximum speed. These conditions were maintained while 266 g. of sulfur were added over a period of 30 minutes. The temperature was raised to 375° F. for two hours. The mixture was then cooled to 200° F. for one hour and air was bubbled through the mixture by means of a glass tube at a moderate rate below that at which splashing takes place. The resulting sulfurized oil was analyzed and found to contain 8.5% sulfur as based on the total composition. A ten gram portion of the sulfurized oil was dissolved in 100 g. of the solvent refined paraffinic lube described in Example 3. The oil solution remained clear with no separation after being tested at 36° F. overnight and for one week at room temperature.

EXAMPLE 5

A useful lubricant for a controlled-slip differential, and which is also useful for lubrication of a traction drive transmission, comprises a blend of the following (all hydrogenations are to at least 98% saturation):

| Volume % | Component | KV210° F. (c.s.) | KV100° F. (c.s.) |
|---|---|---|---|
| 7.0 | Hydrogenated Cosden SH06 Polybutene | 11.04 | 124 |
| 28.0 | Hydrogenated Cosden SH15 Polybutene | 33.5 | 744 |
| 31.6 | Hydrogenated Poly α-Methyl Styrene | 23 | 2463 |
| 21.0 | Hydrogenated Poly α-Methyl Styrene | 4.65 | 39.6 |
| 7.4 | Anglamol 93 (S.P. Additive) | | |
| 3.0 | Amoco 9000 (Dispersant) | | |
| 1.0 | Ultraphos 11, (Low Static Modifier) | | |
| 1.0 | Synthetic Sulfurized Oil of Example 3 | | |

The Ultraphos 11 additive is a surface-active, organic phosphate ester of a linear aliphatic, ethoxylated alcohol.

EXAMPLE 6

The oils of Examples 3 and 4 were tested for a number of properties related to their utility as substitutes for sulfurized sperm oil. These results are shown in the accompanying FIGURE and Table II. The test results indicate that a cosulfurized blend of lard oil and polyisobutylene is a good substitute for sulfurized sperm oil and that the oil made from the C₁₆ olefin (tetraisobutylene) was a superior lubricant additive.

In Table II, the "copper strip" test is performed in accordance with ASTM D-130. A value below 2 is considered adequate for these materials. The weld point is determined using the standard 4 Ball weld test (Fed. 6503). A value below 250 kg. is considered poor. The stick/slip ratio is the ratio of static friction over dynamic friction. A value above 0.85 is considered poor. In the air oxidation test of the FIGURE, a sludge rating of medium is considered adequate and a copper weight loss greater than 50 mg. is considered poor.

TABLE II

| Oil Number In Figure | Material Sulfurized | % S | % "Active" S | Properties 10% in Paraffinic Lube | | 3% in SAE 90 Stick/Slip Ratio |
|---|---|---|---|---|---|---|
| | | | | Copper Strip | Weld Pt. (kg.) | |
| 7 | Triisobutylene & Lard Oil | 8.6 | 0.8 | 1B | 260 | 0.84 |
| 6 | C₁₈ Olefin & Lard Oil | 8.6 | 3.6 | 1B | 270 | 0.84 |
| 5 | Tetraisobutylene & Lard Oil | 8.2 | 1.0 | 1B | 290 | 0.77 |
| 3 | Sulfurized α-Olefin | 8.3 | 0.6 | 1B | — | 1.00 |
| 4 | α-Olefin & Lard Oil | 8.4 | 0.6 | 1A | 260 | 0.75 |

All oils (undiluted) rated "1" in copper strip test.
The "α-Olefin" was predominantly straight chain mono-α-olefin containing from 15-20 carbon atoms.
The "C₁₈ olefin" was "Indopol L-4" consisting mainly of C₁₆ to C₂₀ (average C₁₈) branched, internal olefins.

The invention claimed is:

1. As a composition of matter, a co-sulfurized blend of from 30 to 90 parts by weight of lard oil and from 70 to 10 parts by weight of polyisobutylene containing from 12 to 40 carbon atoms which co-sulfurized blend contains chemically combined therewith from 5 to 25 weight percent of sulfur as based on said blend and wherein said blend contains no more than 18 weight percent of active sulfur.

2. A composition according to claim 1 wherein said co-sulfurized blend contains less than 2.5 weight percent active sulfur.

3. A composition according to claim 1 wherein said co-sulfurized blend contains in the range of 5–18 weight percent active sulfur.

4. A composition according to claim 2 wherein said co-sulfurized blend contains chemically combined therewith from 6 to 11 weight percent of sulfur, as based on said blend.

5. A composition according to claim 3 wherein said co-sulfurized blend contains chemically combined therewith from 16 to 25 weight percent of sulfur, as based on said blend.

6. A composition according to claim 1 wherein said polyisobutylene contains at least 75 weight percent of tetraisobutylene.

7. A composition according to claim 2 wherein said polyisobutylene comprises at least 75 weight percent of tetraisobutylene.

8. A composition according to claim 3 wherein said polyisobutylene comprises at least 75 weight percent of tetraisobutylene.

9. A composition according to claim 4 wherein said polyisobutylene comprises at least 75 weight percent of tetraisobutylene.

10. A composition according to claim 5 wherein said polyisobutylene comprises at least 75 weight percent of tetraisobutylene.

11. A composition comprising a major amount of a mineral oil of lubricating viscosity and a minor lubrication improving quantity of the co-sulfurized blend of claim 1.

* * * * *

UNITED STATES PATENT OFFICE
CERTIFICATE OF CORRECTION

PATENT NO. : 4,166,795
DATED : September 4, 1979
INVENTOR(S) : ALEXANDER D. RECCHUITE It is certified that error appears in the above-identified patent and that said Letters Patent are hereby corrected as shown below:

At Column 2, line 60; insert ---

(C) $-CH = \underset{\underset{CH_3}{|}}{C} - CH_2 - C(CH_3)_3$ or (D) $-CH_2 - \underset{\underset{CH_2}{\|}}{C} - CH_2 - C(CH_3)_3$ or (E) $-CH_2 - \underset{\underset{CH_3}{|}}{C} = CH - C(CH_3)_3$ ---.

At Column 7, line 12; change "Example 3" to ---Example 2---;
line 33; change "Example 6" to ---Example 2---.

Signed and Sealed this

Eighteenth Day of March 1980

[SEAL]

Attest:

SIDNEY A. DIAMOND

Attesting Officer   Commissioner of Patents and Trademarks